United States Patent
Huang et al.

(10) Patent No.: US 12,404,521 B2
(45) Date of Patent: Sep. 2, 2025

(54) StSCI PROTEIN FOR CHANGING SELF-INCOMPATIBILITY OF DIPLOID POTATO MATERIALS

(71) Applicants: AGRICULTURAL GENOMICS INSTITUTE, CHINESE ACADEMY OF AGRICULTURAL SCIENCES, Shenzhen (CN); AGRICULTURAL GENOMICS INSTITUTE AT SHENZHEN, CHINESE ACADEMY OF AGRICULTURAL SCIENCES, Shenzhen (CN)

(72) Inventors: Sanwen Huang, Shenzhen (CN); Ling Ma, Shenzhen (CN); Yi Shang, Shenzhen (CN); Chunzhi Zhang, Shenzhen (CN); Canhui Li, Shenzhen (CN)

(73) Assignees: Agricultural Genomics Institute, Chinese Academy of Agricultural Sciences, Shenzhen (CN); Agricultural Genomics Institute at Shenzhen, Chinese Academy of Agricultural Sciences, Shenzhen (CN)

( * ) Notice: Subject to any disclaimer, the term of this patent is extended or adjusted under 35 U.S.C. 154(b) by 457 days.

(21) Appl. No.: 17/831,509

(22) Filed: Jun. 3, 2022

(65) Prior Publication Data
US 2022/0298526 A1   Sep. 22, 2022

Related U.S. Application Data

(63) Continuation of application No. PCT/CN2020/094344, filed on Jun. 4, 2020.

(30) Foreign Application Priority Data

Dec. 4, 2019   (CN) .......................... 201911230001.4

(51) Int. Cl.
C12N 15/82   (2006.01)
C07K 14/415   (2006.01)

(52) U.S. Cl.
CPC ........ *C12N 15/8287* (2013.01); *C07K 14/415* (2013.01)

(58) Field of Classification Search
None
See application file for complete search history.

(56) References Cited

U.S. PATENT DOCUMENTS

2018/0092316 A1   4/2018   Chintamanani et al.
2022/0267386 A1*  8/2022   Van Der Burgt ...... A01H 6/827

FOREIGN PATENT DOCUMENTS

| CN | 103484474 A | 1/2014 |
|---|---|---|
| CN | 108849471 A | 11/2018 |
| CN | 109548646 A | 4/2019 |
| CN | 109750061 A | 5/2019 |
| CN | 110894539 A | 3/2020 |
| CN | 110938120 A | 3/2020 |
| WO | 2011053135 A2 | 5/2011 |
| WO | 2012144902 A1 | 10/2012 |
| WO | 2018112356 A1 | 6/2018 |
| WO | 2020226499 A1 | 11/2020 |
| WO | 2021109507 A1 | 6/2021 |

OTHER PUBLICATIONS

Guo et al, 2004, Proc. Natl. Acad. Sci. USA 101: 9205-9210; (Year: 2004).*
Ma et al 2021, Nature Communications, 12:4142 (Year: 2021).*
Ames et al 2024, Plant Direct 8, e589 (Year: 2024).*
Eggers et al, Nature Communications 2021, 12:4141 (Year: 2021).*
SEQ ID No. 3 alignment to RH89-039-16; http://spuddb.uga.edu/blast.shtml; accessed Jul. 19, 2024 (Year: 2024).*
SEQ ID No. 1 alignment to RH89-039-16; http://spuddb.uga.edu/blast.shtml; accessed Jul. 19, 2024 (Year: 2024).*
Peterson et al (2016, The Plant Genome 9(3): 1-13). (Year: 2016).*
Alignment 1: SEQ ID No. 2 maps to 'M6 High Confidence Gene Models-cDNA'g26388.tl with 97% sequence identity; Internet Database-Potato Genomics Reource; Online.
Alignment 2: SEQ ID No. 6 maps to m6_v4.1_scafflod_421:32630-33167 with 100% sequence identity; Internet Database-Potato Genomics Resource; Online.
Alignment 3: SEQ ID No. 3 maps to m6_v4.1_scafflod_421:31276-33275 with 100% sequence identity; Internet Database-Potato Genomics Resource; Online.
Translation 4: SEQ ID No. 2 encodesa non-functional protein; Internet Database-Potato Genomics Resource; Online.

(Continued)

*Primary Examiner* — Brent T Page
*Assistant Examiner* — Aleksandar Radosavljevic
(74) *Attorney, Agent, or Firm* — Flener IP & Business Law; Zareefa B. Flener

(57) ABSTRACT

Provided is a StSCI protein for changing the self-incompatibility of diploid potato materials, wherein the amino acid sequence of the StSCI protein includes or consists of the following sequence: 1) the amino acid sequence represented by SEQ ID NO: 1; or 2) a functional homologous sequence having at least 95% sequence identity with the amino acid sequence represented by SEQ ID NO: 1; or 3) a protein in which one or more (e.g., 1-10) amino acids are added, deleted, or replaced in the amino acid sequence represented by SEQ ID NO: 1 and has the activity of inhibiting self-incompatibility. The advantage of the application is that the StSCI protein may inhibit the cytotoxicity of multiple types of S-RNase, which is hereditary and fundamentally overcomes the defect of self-incompatibility of diploid potatoes, thereby facilitating to realize the cultivation of a high-generation homozygous inbred line of diploid potatoes.

9 Claims, 1 Drawing Sheet
Specification includes a Sequence Listing.

(56) References Cited

OTHER PUBLICATIONS

S.H. Jansky, et al.; M6: A Diploid Potato Inbred Line for Use in Breeding and Genetics Research; Journal of Plant Registrations-Germplasm; Feb. 21, 2014; pp. 195-199; vol. 8(2); USA.
Courtney P. Leisner, et al.; Genome sequence of M6, a diploid inbred clone of the high-glycoalkaloid-producing tuber-bearing potato species *Solanum chacoense*, reveals residual heterozygosity; The Plant Journal; 2018; pp. 562-570; vol. 94(3); England.
The Potato Genome Sequencing Consortium; Genome sequence and analysis of the tuber crop potato; Nature; Jul. 2011; pp. 189-195; vol. 475; England.
Chalermpol Phumichai, et al.; Toward the development of highly homozygous diploid potato lines using the self-compatibility controlling Sli gene; Genome; Nov. 2005; pp. 977-984; vol. 48; Canada.
Kazuyoshi Hosaka and Rena Sanetomo; Creation of a highly homozygous diploid potato using the S locus inhibitor (Sli) gene; Euphytica; Oct. 7, 2020; pp. 1-16; vol. 216:169; Netherlands.
Communication Pursuant to Rule 114(2) EPC for serial No. 20895309. 1; Issued Jul. 11, 2022.
International Search Report, International application No. PCT /CN2020/094344, Date of mailing Sep. 10, 2020.
PCT Written Opinion of the International Searching Authority, International application No. PCT/CN2020/094344, International filing date, Jun. 4, 2020, date of mailing Sep. 10, 2020.
Mingwang Ye et al. Title of the article: Generation of self-compatible diploid potato by knockout of S-RNase, Nature Plants, vol. 4, pp. 651-654, Published Aug. 13, 2018.
Felix Enciso-Rodriguez et al., Title of the article: Overcoming Self-Incompatibility in Diploid Potato Using CRISPR-Cas9, Frontiers in Plant Science, vol. 10, pp. 1-12, Published Apr. 2, 2019.
Locus XM, Title of the article: Predicted Solanum tuberosum F-box protein PP2-B10-like (LOC107061040), mRNA, Published Jan. 5, 2016.
Title of the article: SubName Full=F-box protein PP2-B10, Published Dec. 23, 2015.
Zhang et al., Title of the article: The genetic basis of inbreeding depression in potato, Nature Genetics, vol. 51, pp 374-378 Published Jan. 14, 2019.
Chunzhi Zhang et al., Title of the article: Studies of self-incompatibility and inbreeding depression in diploid potato, vol. 5, pp. D047-32 Published May 15, 2019.
Li Ying, et al., Title of the article: Prospects of Diploid Hybrid Breeding in Potato, vol. 27, pp. 96-99, Published Apr. 25, 2013.
Predicted Solanum pennellii F-box protein PP2-B10-like (LOC107005456), mRNAb Published Dec. 23, 2015.
The State Intellectual Property Office of People's Republic of China, First Office Action, Application No. or Publication No. 201911230001.4, dated Dec. 30, 2020.
Ling, Ma et al, A nonS-locus F-box gene breaks self-incompatibility in diploid potatoes, Nature Communications, Published online Jul. 6, 2021.
Eupropean Search Report, Application No./Patent No. 20895309. 1-1118 / 4023665 PCT/CN202009434, Sep. 30, 2022.
Extended European Search Report for Serial No. EP 20895309; issued Sep. 1, 2023.
European Patent Office Communication pursuant to Rule 114(2), Third Party Observation for Serial No. EP 20895309; Issued Oct. 11, 2022.
Kazuyoshi Hosaka and Robert E. Hanneman, Jr.; Genetics of self-compatibility in a self-incompatibl wild diploid potato species *Solanum chacoense*. 2. Localization of an S locus inhibitor (Sli) gene on the potato genome using DNA markers; Euphytica; article; Sep. 1998; p. 265-271; vol. 103; Netherlands.
Ling Ma, et al.; A nonS-locus F-box gene breaks self-incompatibility in diploid potatoes; Nature Communications; article; Jul. 6, 2021; pp. 1-8; vol. 12; Online.
R.K. Birhman and K. Hosaka; Production of inbred progenies of diploid potatoes using an S-locus inhibitor (Sli) gene, and their characterization; Genome; article; May 11, 2000; pp. 495-502; vol. 43; Canada.
Ernst-Jan Eggers, et al.; Neofunctionalisation of the Sli gene leads to self-compatibility and facilitates precision breeding in potato; Nature Communications; article; Jul. 6, 2021; pp. 1-9; vol. 12; Online.

* cited by examiner

SEQUENCE LISTING

```
<160> NUMBER OF SEQ ID NOS: 6

<210> SEQ ID NO 1
<211> LENGTH: 266
<212> TYPE: PRT
<213> ORGANISM: Unknown
<220> FEATURE:
<223> OTHER INFORMATION: the amino acid sequence of the StSCI protein

<400> SEQUENCE: 1

Met Asp Tyr Phe Leu Leu Leu Pro Glu Gly Cys Val Cys Asp Ile Leu
1               5                   10                  15
```

Ser Phe Thr Ser Pro Lys Asp Val Val Ile Ser Ser Ala Ile Ser Arg
            20                  25                  30

Gly Phe Asn Ser Ala Ala Glu Ser Asp Val Ile Trp Val Lys Phe Leu
        35                  40                  45

Pro Asp Asp Tyr Glu Asp Ile Ile Ser Arg Tyr Val Ser Pro Arg Ile
 50                  55                  60

Tyr Pro Ser Lys Lys Glu Leu Tyr Phe Ser Leu Cys Asp Phe Pro Val
 65                  70                  75                  80

Leu Met Asp Gly Gly Lys Leu Ser Phe Ser Leu Asp Lys Lys Thr Gly
                 85                  90                  95

Lys Lys Cys Phe Met Ile Ser Ala Arg Glu Leu Ala Ile Ser Trp Gly
                100                 105                 110

Val Asp Thr Pro Trp Tyr Trp Glu Trp Ile Ser His Pro Asp Ser Arg
            115                 120                 125

Phe Ser Glu Val Ala His Leu Lys Gly Val Ser Trp Leu Asp Ile Arg
130                 135                 140

Gly Thr Ile Gly Thr Gln Ile Leu Ser Lys Arg Thr Lys Tyr Val Val
145                 150                 155                 160

Tyr Leu Val Phe Lys Leu Ala Lys Asp His Asp Gly Leu Glu Ile Ala
                165                 170                 175

Asn Ala Phe Val Arg Phe Val Asn Arg Val Ser Asp Lys Asp Ala Glu
                180                 185                 190

Glu Arg Ala Ser Val Val Ser Leu Val Gly Lys Arg Val Arg Arg
            195                 200                 205

Lys Arg Asn Val Lys Arg Pro Arg Lys Arg Val Asp Gly Trp Met Glu
            210                 215                 220

Ile Glu Leu Gly Asn Phe Ile Asn Asp Thr Gly Asp Gly Asp Val
225                 230                 235                 240

Glu Ala Arg Leu Met Glu Ile Thr Arg Leu His Gly Lys Gly Leu
                245                 250                 255

Ile Val Gln Gly Ile Glu Phe Arg Pro Glu
                260                 265

<210> SEQ ID NO 2
<211> LENGTH: 801
<212> TYPE: DNA
<213> ORGANISM: Unknown
<220> FEATURE:
<223> OTHER INFORMATION: the nucleotide sequence encoding the StSCI
      protein

<400> SEQUENCE: 2
atggactatt tcctattgct accagaaggt tgtgtttgtg atattctctc ctttacttcc      60
ccgaaagatg tcgtgatttc atccgcgatc tctcggggat tcaactctgc tgctgaatcc     120
gacgttattt gggtaaagtt tttaccagat gattatgaag atattatctc gagatatgtc     180
tccccgcgga tttatccgtc taaaaaggag ctttacttta gtctatgtga cttccctgtt     240
ctaatggatg gaggcaaatt gagcttttca cttgataaga aaacaggcaa gaaatgtttt     300
atgatatcag ctagagaact tgctatttca tggggagttg atacaccatg gtattgggaa     360
tggatttctc atcccgactc cagattttcg gaagtggcac atctcaaggg tgtaagttgg     420
ctagacatac gaggcacgat tggaacacaa atattgtcga aagaaccaa atatgttgtt      480 tatttggtgt tcaaattggc aaaggatcat gatggactag aaattgctaa tgcatttgtt     540
agatttgtga atcgtgtgag cgataaagat gccgaggaac gagctagtgt cgtgagtcta     600

```
gtcggaaaaa gggttaggag acgcaaacgt aacgtaaaac gtccacgaaa aagagtcgat    660
ggatggatgg aaatagaatt gggaaatttt atcaacgata caggagatga tggagatgtt    720
gaagcgcgat tgatggagat tacgcggctt catggaaaag gtggccttat tgttcaagga    780
attgaattta gaccagaatg a                                              801
```

```
<210> SEQ ID NO 3
<211> LENGTH: 2000
<212> TYPE: DNA
<213> ORGANISM: Unknown
<220> FEATURE:
<223> OTHER INFORMATION: the nucleotide sequence of a promoter for
      regulating the nucleotide sequence encoding the StSCI protein

<400> SEQUENCE: 3 tcattttaa aaaacagcgt attcccatat ggtggagatg gtactactgg tgttgtcctg      60
ttgcctggac cttgtatggt ttggttgcat cacaatttgg agatcttcag aacaaactta    120
ctgatgagga aacagtggaa cattttttga gacgttactt cggcttcaag catgattttc    180
ttccaatagt tgcagtcgcg attgttgggt acactgttct ttttggcttc acatttgctt    240
tcgctattaa ggcattcaac ttccaaacga gataaaaaga cattacctgc tgaagatgta    300
gtaaagacaa cgtgtgaaac gttctctcca ctgctcgtga aatggggaag acgcggttag    360
tataaggaat ttttctcgag ctcaagtacg agcaagagat tgattttgaa agtactgtat    420
atagattacc acttgaacaa gggtatgttc tgttattatt attatttttt atgaatttca    480
agttcatttt tctgtgtaag agatagtaat ttgttaatgt tgaagtacta ttctgttact    540
atctggtgtt tcttgtactt ttgttgtgtc tttttctgaa ctgctttgga ttatttttct    600
cgagtcgagg atctatcgga agaagacttt ctacctctga ggtaagagta agtttgctt     660 acactctacc cttcccatac tccactttgt gggggagaca catggtatgt tgttcttata    720
gttacaacta taagaaatta atgaaatgat gaatgtaaga attgtgaat attgcttttc     780 gggaactgcc acaactgtgg tgcgagaatg agacttctct agtgttaact aaacaacaag    840
tctttggttt gaattcggag aatggagaaa ttccttggtcg ggaacgctcc ttgataaatg    900
gaccttagat gatgctaatc ttaaattagt cgggccagta aatttcgaat cttccaagac    960
atttcatgtt ttaattcact aaaaaggaaa gacaaaaaat ttcaaactca aacatttca   1020 tgtttagtat tattggaata tcttcctcca catgagttgt ttgtttggtg tatctaagca   1080
atatcaattc tttaatttta ttttttttg gaaataaaat gtacatatgt gagaactaga   1140 taaaataat gaaaataaa caaaaatgat tttttaaaa ataaaataaa attaaatatt     1200
ttcacttcca ttaggccaaa agggtatatc taggctattt gtgtaatagt ataggtatgt   1260
atgagccatt tttataacga ggtatgtatc agctctaaat tatatgacct tttcacttat   1320
tatattcata ctggagaagt aaaaatgaac aaaacaatat ttaaccgcag tgccggctca   1380
atgcttataa aaattaggca tatgccttag gcccccaatt ttaggggggc ctcaaatttt   1440
taccaacaat aaattatgtg ttaattttt tatagaaaa aattaattat ttaagataaa    1500
tgtacttttc atatatatat tattttattc tccttaacct caatcaaata gaagaaatca   1560
agaaaaacgt tgttttgtct tcttacactc tcttcactta ctctcgcgtt gtaatttct    1620 ataccccttt tatactctat gtaagttaga gctctatcaa aaatatgaat caatagtaaa   1680
actaatgtgt tggataaagc gaattacaag cctgtttaga ttgacttatg ttatgtgctt   1740
ttaaataaaa aaagaagttt ataagcagtt ttgtcaactt attacttata gaataatgtt   1800
```

```
aacaatttat ttaataattg cctcagctaa aagattttag gcctttaatt taaattttgt    1860
tttaggcctc caaatacgtt gagccgcccc tgcttaaccg tcgagacata tgaagtgtaa    1920
caacttttca acaaactttt ctcagtttgc tttatataaa gaaaaaaaat tcacaaaact    1980
tcaaattcaa ttttccaata                                                2000

<210> SEQ ID NO 4
<211> LENGTH: 29
<212> TYPE: DNA
<213> ORGANISM: Artificial Sequence
<220> FEATURE:
<223> OTHER INFORMATION: upstream primer

<400> SEQUENCE: 4
atggactatt tcctattgct accagaagg                                        29

<210> SEQ ID NO 5
<211> LENGTH: 29
<212> TYPE: DNA
<213> ORGANISM: Artificial Sequence
<220> FEATURE:
<223> OTHER INFORMATION: downstream primer

<400> SEQUENCE: 5
tcattctggt ctaaattcaa ttccttgaa                                        29

<210> SEQ ID NO 6
<211> LENGTH: 538
<212> TYPE: DNA
<213> ORGANISM: Unknown
<220> FEATURE:
<223> OTHER INFORMATION: insert sequence

<400> SEQUENCE: 6 cagggcggc tcaacgtatt tggaggccta aacaaaatt taaattaaag gcctaaaatc        60
ttttagctga ggcaattatt aaataaattg ttaacattat tctataagta ataagttgac     120
aaaactgctt ataaacttct tttttattt aaaagcacat aacataagtc aatctaaaca     180
ggcttgtaat tcgctttatc caacacatta gttttactat tgattcatat ttttgataga    240
gctctaactt acatagagta taaaggggt atagaaaatt acaacgcgag agtaagtgaa    300
gagagtgtaa aagacaaaa caacgttttt cttgatttct tctatttgat tgaggttaag    360
gagaataaaa taatatatat atgaaaagta catttatctt aaataattaa ttttttctat    420
aaaaaaaatt aacacataat ttattgttgg taaaaatttg aggcccccct aaaattgggg    480
gcctaaggca tatgcctaat ttttataagc attgagccgg cactgcggtt aaatattg      538
```

StSCI PROTEIN FOR CHANGING SELF-INCOMPATIBILITY OF DIPLOID POTATO MATERIALS

CROSS-REFERENCE

This application is a continuation of International Application No. PCT/CN2020/094344, filed on Jun. 4, 2020, which claims priority to Chinese Patent Application No. 201911230001.4, filed on Dec. 4, 2019. The disclosures of the aforementioned applications are hereby incorporated by reference in their entireties.

The contents of the electronic sequence listing (Sequence Listing. txt; Size: 8,082 bytes; and Date of Creation: Apr. 14, 2025) is herein incorporated by reference in its entirety.

TECHNICAL FIELD

This application relates to the technical field of genetic breeding, in particular to a StSCI protein for changing the self-incompatibility of diploid potato materials.

BACKGROUND

Diploid potato seed breeding refers to the cultivation of high-generation inbred lines basically homozygous in their genomes through continuous self-crossing of multiple generations, and then the inbred lines are crossed with each other to produce F1 hybrid seeds with heterosis, and the F1 hybrid seeds are used to achieve potato planting plan. Compared with the traditional tetraploid tuber propagation, the diploid potato seed breeding has the following outstanding advantages: firstly, a parent of the traditional tetraploid potato includes four sets of highly heterozygous chromosomes with complex genetic background, and has low frequency of excellent traits, accordingly the breeding efficiency is low, and it is difficult to breed good varieties; while a parent of diploid potato material includes only two sets of chromosomes with relatively simple genetic background, and it may well overcome the defects of tetraploid. The staple food crops such as rice and corn are all diploid hybrid breeding, the breeding experience of these crops may provide a good technical reference for the development of seed breeding of diploid potato. Secondly, compared to traditional tuber propagation, seed propagation has many advantages. The efficiency of tuber propagation is low, and one seed potato tuber may only produce about 10 tubers. The annual production of seed potato tuber requires a lot of land, the seed potato tuber is not easy to store and transport and it is easy to accumulate various diseases and insect pests. Seed reproduction may effectively overcome the above shortcomings, the reproduction efficiency of seed reproduction is as high as 1:5000-10000, the seed is small in size and light in weight, it is easy to store and transport and basically does not carry pests and diseases.

Although seed breeding of diploid potato has outstanding advantages, the self-incompatibility of diploid potato restricts the development of seed breeding, and it is difficult to obtain homozygous parent material through multiple generations of self-crossing. Therefore, it is of important practical significance to break the self-incompatibility of diploid potatoes.

Studies have shown that potato self-incompatibility belongs to gametophytic self-incompatibility, which is controlled by the S-locus on chromosome 1. When its own pollen or pollen with the same S haplotype falls on the stigma, the pollen tube cannot extend to the ovule to complete the fertilization process, i.e., self-pollination cannot produce seeds. The S-locus includes at least two types of genes; one type is specifically expressed in the pistil and determines the self-incompatibility of the pistil, so it is called the pistil S factor, which encodes a type of secreted RNase named as S-RNase; another type determines the self-incompatibility of stamens, and is called as stamen S factor, which encodes a type of F-box protein named SLF (S-Locus F-box) protein. S-RNase is expressed in the conduction tissue cells of the pistil style, and is secreted into the conduction tube of the style after expression. When the pollen germinates on the stigma, the pollen tube extends into the conduction tube, and the free S-RNase enters the pollen tube. S-RNase may degrade the rRNA in the pollen tube and depolymerize the cytoskeleton in the pollen tube, eventually causing the death of pollen tube cells, which has a cytotoxic effect and terminates the extension of the pollen tube. The SLF protein expressed in the pollen tube has a certain degree of detoxification, by forming an SCF complex with other proteins, it may specifically recognize and ubiquitinate S-RNase. The ubiquitinated S-RNase is degraded by 26S proteasome. However, a specific SLF protein may only relieve the cytotoxicity of one or several S-RNases, and certainly cannot recognize the S-RNase produced by its own pistil. Therefore, self-crossing of diploid potatoes is incompatible.

The existing methods for creating self-compatible diploid potato materials mainly use a self-compatible diploid wild potato S. chacoence as the male parent, after hybridizing with other diploid potato material, the resulting offspring are identified whether they are self-compatible by massive pollination work. The main disadvantage of this method is that: since this wild potato has a relatively distant relationship with the cultivated diploid potato, the hybrid offspring will introduce many wild undesirable traits, such as smaller potato tube, increased solanine content in potato tube, and longer stolons; multiple generations of backcrossing is needed to eliminate these wild undesirable traits, which consumes a lot of time and human resources. Therefore, there is an urgent need to develop better ways to overcome the self-incompatibility of potatoes.

SUMMARY

In view of this, the present application provides a StSCI protein for changing the self-incompatibility of diploid potato materials. StSCI protein may inhibit the cytotoxicity of a variety of S-RNases, thereby overcoming the self-incompatibility defect of diploid potato materials, and obtaining a new kind of self-compatible material for diploid potato to realize the seed breeding of diploid potato.

In one aspect, this application provides a StSCI protein for changing the self-incompatibility of diploid potato materials, wherein the amino acid sequence of the StSCI protein includes or consists of the following sequence:
1) the amino acid sequence represented by SEQ ID NO: 1; or
2) a functional homologous sequence having at least 95% sequence identity with the amino acid sequence represented by SEQ ID NO: 1; or
3) a protein in which one or more (e. g., 1-10) amino acids are added, deleted, or replaced in the amino acid sequence represented by SEQ ID NO: 1 and has the activity of inhibiting self-incompatibility.

Through large-scale resource screening in this application, it is found that diploid potato material RH89-039-16 is self-compatible, i.e., self-pollination may produce seeds.

The pollen of RH89-039-16 is used to pollinate the originally self-incompatible potato diploid material PI 225689, and the seeds are harvested as the F1 generation. The self-compatibility traits of the F1 generation plants are investigated, and it is found that the self-compatible plants and self-incompatible plants respectively account for half of them, indicating that the self-compatibility genes in RH89-039-16 are in a heterozygous state; while RH89-039-16 exhibits self-compatibility traits, indicating that the gene for controlling self-compatibility of RH89-039-16 is dominant. This dominant gene is named as the self-compatibility inducer abbreviated as StSCI gene.

A protein encoded by the StSCI gene is named as StSCI protein. StSCI protein may degrade a variety of S-RNases, thereby preventing S-RNase from degrading rRNA in the pollen tube and depolymerizing the cytoskeleton in the pollen tube, so as to ensure the normal extension of the pollen tube and overcome the self-incompatibility of the diploid potato material.

In one embodiment of the present application, the amino acid sequence of the StSCI protein is the amino acid sequence represented by SEQ ID NO: 1.

In one embodiment of the present application, the amino acid sequence of the StSCI protein is a functional homologous sequence having at least 95% sequence identity with the amino acid sequence represented by SEQ ID NO: 1. The functional homologous sequence with identity includes, but is not limited to, an amino acid sequence having at least 95% or more, 95.5% or more, 96% or more, 96.5% or more, 97% or more, 97.5% or more, 98% or more, 98.5% or more, 99% or more, 99.1% or more, 99.2% or more, 99.3% or more, 99.4% or more, 99.5% or more, 99.6% or more, 99.7% or more, 99.8% or more, 99.9% or more identity with the amino acid represented by SEQ ID NO: 1.

In one embodiment of the present application, the amino acid sequence of the StSCI protein is a protein in which one or more (e. g., 1, 2, 3, 4, 5, 6, 7, 8, 9, or 10) amino acids are added, deleted, or replaced in the amino acid sequence represented by SEQ ID NO: 1 and has the activity of inhibiting self-incompatibility.

Another aspect of the present application provides a nucleotide sequence encoding the above StSCI protein.

Further, the nucleotide sequence encoding the above StSCI protein includes or consists of the following sequence:
1) the nucleotide sequence represented by SEQ ID NO: 2; or
2) a complementary sequence, a degenerate sequence, or a homologous sequence of the nucleotide sequence represented by SEQ ID NO: 2;

Preferably, the homologous sequence is a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 2, and encoding a protein with the activity of inhibiting self-incompatibility, or a corresponding cDNA molecule thereof; or
3) a nucleotide sequence hybridizing with the nucleotide sequence of SEQ ID NO: 2 under stringent conditions and encoding a protein with the activity of inhibiting self-incompatibility.

In one embodiment of the present application, the nucleotide sequence encoding the above StSCI protein is the nucleotide sequence represented by SEQ ID NO: 2.

In one embodiment of the present application, the homologous sequence includes, but is not limited to, a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 2, or a corresponding cDNA molecule thereof.

In one embodiment of the present application, the nucleotide sequence encoding the StSCI protein is a nucleotide sequence hybridizing with the nucleotide sequence of SEQ ID NO: 2 under stringent conditions and encoding a protein with the activity of inhibiting self-incompatibility.

Exemplarily, the "stringent conditions" as used herein refer to conditions under which a probe will hybridize to its target sequence to a detectable extent beyond hybridization with other sequences (such as at least 2 times the background). Stringent conditions are sequence-dependent, and vary from different environments. By controlling the stringency of hybridization and/or washing conditions, a target sequence that is 100% complementary to the probe may be identified. Alternatively, stringent conditions may be adjusted to allow some sequence mismatches, so that a lower degree of similarity is detected. These nucleotide sequences that hybridize under stringent conditions may be used, for example, to express the variant protein of SEQ ID NO: 1 or may be used as primers, probes, exogenous donor sequences, guide RNA, antisense RNA, shRNA and siRNA.

In one embodiment of the present application, as for the degenerate sequence, after changing one or more nucleotides in the nucleotide sequence of SEQ ID NO: 2, the position of the changed nucleotide(s) in this sequence corresponds to the same type of the encoded amino acid, and the amino acid sequence of the encoded StSCI protein remains unchanged.

Another aspect of the present application provides a promoter for regulating the nucleotide sequence encoding the StSCI protein, wherein the nucleotide sequence of the promoter includes or consists of the following sequence:
1) the nucleotide sequence represented by SEQ ID NO: 3; or
2) a functional homologous sequence having at least 90% sequence identity with the nucleotide sequence represented by SEQ ID NO: 3; or
3) a polynucleotide hybridizing to the nucleotide sequence represented by SEQ ID NO: 3 under stringent conditions or a complementary sequence thereof.

The promoter is a DNA sequence fragment recognized, bound and started transcription by RNA polymerase, and it includes conserved sequences required for RNA polymerase specific binding and transcription initiation; most of the conserved sequences are located upstream of the transcription initiation point of structural genes, and the promoter itself is not transcribed.

The sequence length of the promoter for regulating the nucleotide sequence encoding the StSCI protein cannot be accurately determined, as long as the promoter includes the core promoter fragment, it may allow the gene encoding the StSCI protein to express.

In one embodiment of the present application, the nucleotide sequence of the promoter is represented by SEQ ID NO: 3. The promoter region includes a sequence of 538 bp in length, which is represented by SEQ ID NO: 6. SEQ ID NO: 6 is located at 100 bp upstream of the initiation codon of the StSCI gene, and includes an annotated promoter core element. The missing of SEQ ID NO: 6 sequence causes the StSCI gene not to be expressed in conventional diploid potato materials, such as PI 225689, S15-65, etc., and that is also the reason for the incompatibility of conventional diploid materials. In the diploid potato material RH89-039-16, the promoter region of the StSCI gene is represented by SEQ ID NO: 3, and includes the sequence of SEQ ID NO: 6, thus the StSCI gene in the pollen of RH89-039-16 has a high expression level and may effectively relieve the cytotoxicity of S-RNase. Therefore, RH89-039-16 is self-compatible.

In one embodiment of the present application, the nucleotide sequence of the promoter is the nucleotide sequence represented by SEQ ID NO: 3.

In one embodiment of the present application, the nucleotide sequence of the promoter is a functional homologous sequence having at least 90% sequence identity with the nucleotide sequence represented by SEQ ID NO: 3.

Preferably, the homologous sequence is a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 3.

In one embodiment of the present application, the nucleotide sequence of the promoter is a polynucleotide hybridizing with the nucleotide sequence represented by SEQ ID NO: 3 under stringent conditions or a complementary sequence thereof.

Exemplarily, the "stringent conditions" as used herein refer to conditions under which a probe will hybridize to its target sequence to a detectable extent beyond hybridization with other sequences (such as at least 2 times the background). Stringent conditions are sequence-dependent, and vary from different environments. By controlling the stringency of hybridization and/or washing conditions, a target sequence that is 100% complementary to the probe may be identified. Alternatively, stringent conditions may be adjusted to allow some sequence mismatches, so that a lower degree of similarity is detected.

Further, the nucleotide sequence of the promoter is operably linked to the heterologous encoding sequence.

In one embodiment of the present application, the promoter nucleotide sequence provided in the self-compatible diploid potato RH89-039-16, may be operably linked to the StSCI gene provided by other type of self-incompatible diploid potato (i.e., a heterologous sequence encoding StSCI protein), then a recombinant gene fragment containing the promoter region and the heterologous coding region may be constructed outside the cell for subsequent genetic engineering operations.

Another aspect of the present application provides PCR primers for amplifying the nucleotide sequence encoding the StSCI protein.

Herein, the nucleotide sequence of the PCR product for amplifying the nucleotide sequence encoding the StSCI protein is not specifically limited, as long as the primer may specifically amplify the nucleotide sequence encoding the StSCI protein.

In a preferred embodiment of the present application, the PCR primers are an upstream primer and/or a downstream primer, wherein the upstream primer contains the sequence of 5'-ATGGACTATTTCCTATTGCTACCAGAAGG-3' (SEQ ID NO: 4); and the downstream primer contains the sequence of 5'-TCATTCTGGTCTAAATTCAATTCCTTGAA-3' (SEQ ID NO: 5).

Using a primer pair composed of an upstream primer and a downstream primer for PCR amplification, double-stranded DNA of the nucleotide sequence encoding the StSCI protein may be amplified. Preferably, the above primer pair is used for PCR amplification, and the band of the amplified StSCI gene has good specificity and the miscellaneous bands is few.

Another aspect of the application provides a vector containing the nucleotide sequence encoding the StSCI protein and the promoter.

The nucleotide sequence composed of the nucleotide sequence encoding the StSCI protein and the promoter has the same restriction sites or homologous recombination sites with the nucleotide sequence of the vector, so as to form a recombinant expression vector. The specific type of the vector is not limited, as long as it may successfully construct a recombinant expression vector, and the expression vector may be mediated into a diploid potato by engineered bacteria so as to normally express the StSCI gene.

Further, the vector includes, but is not limited to, one or a combination of more selected from the group consisting of: pCAMBIA1301, pCAMBIA1302, pCAMBIA1303, pCAMBIA1304, pCAMBIA1305, pCAMBIA2300, pCAMBIA2301, pCAMBIA3300, pCAMBIA3301, pCAMBIA1380, pCAMBIA1390, pCAMBIA super1300, pCAMBIA super1300-GFP, pCAMBIA super1300-EGFP, pCAMBIA super1390-GFP.

In a preferred embodiment of the present application, provided is a vector containing the nucleotide sequence encoding the StSCI protein and a heterologous promoter.

It should be noted that, the "heterologous promoter" herein means that the promoter for regulating the StSCI gene is not derived from the self-compatible diploid potato that provides the StSCI gene, and its source may include, but is not limited to, other type of self-compatible diploid potatoes, or promoters commonly used in plant genetic engineering.

Further, the heterologous promoter includes but is not limited to: CaMV35S promoter, NOs promoter, or Ocs promoter.

In a preferred embodiment of the present application, the heterologous promoter is CaMV35S promoter.

Further, the vector includes, but is not limited to, one or a combination of more selected from the group consisting of: pCAMBIA1301, pCAMBIA1302, pCAMBIA1303, pCAMBIA1304, pCAMBIA1305, pCAMBIA2300, pCAMBIA2301, pCAMBIA3300, pCAMBIA3301, pCAMBIA1380, pCAMBIA1390, pCAMBIA super1300, pCAMBIA super1300-GFP, pCAMBIA super1300-EGFP, pCAMBIA super1390-GFP.

In a preferred embodiment of the present application, the vector is pCAMBIA1301.

Another aspect of the present application provides a microorganism or plant cell into which the nucleotide sequence encoding the StSCI protein has been introduced.

Another aspect of the present application provides a microorganism or plant cell into which the vector is introduced.

The nucleotide sequence and/or vector encoding the StSCI protein according to the application, may be introduced into a microorganism or plant cell. Herein, the "microorganism" refers to a specific microorganism into which the StSCI gene is introduced, and also includes the offspring of the microorganism carrying the vector. The microorganism may be any prokaryotic or eukaryotic cell organism.

Further, the StSCI gene may be expressed in microorganisms, including but not limited to *Agrobacterium, Bacillus subtilis, Bacillus subtilis, Escherichia coli, Lactobacillus*, and insect cells, or other microorganisms suitable to be host cells commonly used by those skilled in the art.

Furthermore, the microorganism is preferably *Agrobacterium*. The strains of *Agrobacterium* include but are not limited to: *Agrobacterium* LBA440, *Agrobacterium* EHA101, *Agrobacterium* EHA105, and *Agrobacterium* GV3101.

Further, methods for introducing the StSCI gene into a host cell in vivo and in vitro include, but are not limited to, electroporation, polyethylene glycol (PEG) transformation, lipofection, heat shock, calcium phosphate precipitation, virus mediation, and microinjection.

Another aspect of this application provides a method for expressing a target gene in a plant. The nucleotide sequence encoding the StSCI protein, or the vector, or the microorganism is transferred into a plant to obtain the expression of the target gene.

Further, the plant includes but is not limited to: diploid potato, rice, wheat, corn, soybean, *Arabidopsis*, tobacco, tomato, potato, rape, radish, cabbage, or onion.

Further, the plant also includes plant parts such as explants, including but not limited to: cuttings, tissue culture, cell suspension, and callus.

Further, the plant is more preferably a diploid potato.

Another aspect of the present application provides a method for producing a self-compatible diploid potato, which includes allowing the diploid potato plant to express the StSCI protein.

Further, the nucleotide sequence encoding the StSCI protein, or the vector, or the microorganism is transferred into the diploid potato to express the StSCI protein in the diploid potato.

Furthermore, the microorganism is preferably *Agrobacterium*. The strains of *Agrobacterium* include but are not limited to: *Agrobacterium* LBA440, *Agrobacterium* EHA101, *Agrobacterium* EHA105, and *Agrobacterium* GV3101.

Further, the vector includes, but is not limited to, one or a combination of more selected from the group consisting of: pCAMBIA1301, pCAMBIA1302, pCAMBIA1303, pCAMBIA1304, pCAMBIA1305, pCAMBIA2300, pCAMBIA2301, pCAMBIA3300, pCAMBIA3301, pCAMBIA1380, pCAMBIA1390, pCAMBIA super1300, pCAMBIA super1300-GFP, pCAMBIA super1300-EGFP, pCAMBIA super1390-GFP.

Further, methods for introducing the StSCI gene into a host cell in vivo and in vitro include, but are not limited to, electroporation, polyethylene glycol (PEG) transformation, lipofection, heat shock, calcium phosphate precipitation, virus mediation, and microinjection.

In a particular embodiment of the present application, a method for producing self-compatible diploid potatoes, the pCAMBIA1301 vector carrying the nucleotide sequence encoding the StSCI protein and the homologous promoter is transformed into a diploid potato by using *Agrobacterium*, so that the StSCI protein is expressed in the diploid potato in large quantity.

In a particular embodiment of the present application, a method for producing self-compatible diploid potatoes, the pCAMBIA1301 vector carrying the nucleotide sequence encoding the StSCI protein and the CaMV35S promoter is transformed into a diploid potato by using *Agrobacterium*, so that the StSCI protein is expressed in the diploid potato in large quantity.

Another aspect of the application provides diploid potato plants, potato tubers, and potato leaves obtained by the method for producing a self-compatible diploid potato.

In a particular embodiment of the present application, the diploid potato includes the pCAMBIA1301 vector containing the nucleotide sequence encoding the StSCI protein and the homologous promoter. The vector is introduced into the diploid potato, under activation of the homologous promoter the StSCI gene may express the StSCI protein, thereby inhibiting the cytotoxic effect of a variety of S-RNases, so that the diploid potato has self-incompatibility.

In a particular embodiment of the present application, the diploid potato includes the pCAMBIA1301 vector containing the nucleotide sequence encoding the StSCI protein and the heterologous CaMV35S promoter. The vector is introduced into the diploid potato, under activation of the heterologous CaMV35S promoter the StSCI gene may express the StSCI protein, thereby degrading a variety of S-RNases, so that the diploid potato has self-compatibility.

Another aspect of the present application provides a method for breeding diploid potato, which includes utilizing a self-compatible diploid potato plant containing the nucleotide sequence encoding the StSCI protein, or a diploid potato plant obtained by the method for expressing a target gene in a plant, or a diploid potato plant obtained by the method for producing a self-compatible diploid potato to perform self-crossing or hybridize with other diploid potato plant.

In a particular embodiment of the present application, a self-compatible diploid potato material (e.g., RH89-039-16) itself containing the StSCI gene is used for self-crossing, wherein the pollen produced by the stamens of the diploid potato pollinates the pistils of itself, thereby producing the diploid potato offspring and the diploid potato seeds with self-compatibility by self-crossing.

In a particular embodiment of this application, the pollen of a self-compatible diploid potato material (e.g., RH89-039-16) itself containing the StSCI gene is used for pollinating other diploid potato material (such as a self-incompatible potato material), introducing the chromosome fragment normally expressing StSCI gene in the diploid potato material RH89-039-16 into other diploid potato material by hybridization, thereby producing the diploid potato offspring and the diploid potato seeds with self-compatibility by hybridization.

Another aspect of the present application provides a method for breeding diploid potato, which includes doubling a self-compatible diploid potato plant containing the nucleotide sequence encoding the StSCI protein, or a diploid potato plant obtained by the method for expressing a target gene in a plant, or a diploid potato plant obtained by the method for producing a self-compatible diploid potato into a tetraploid plant, then hybridizing with other tetraploid potato plant, and then reducing into a diploid potato plant.

Another aspect of the present application provides a method for breeding tetraploid potato, which includes doubling a self-compatible diploid potato plant containing the nucleotide sequence encoding the StSCI protein, or a diploid potato plant obtained by the method for expressing a target gene in a plant, or a diploid potato plant obtained by the method for producing a self-compatible diploid potato into a tetraploid plant, then hybridizing with other tetraploid potato plant.

Another aspect of the application provides a food prepared from a diploid potato plant obtained by a method for producing a self-compatible diploid potato, or a diploid potato plant obtained by the method for breeding a diploid potato, or a tetraploid potato plant obtained by the method for breeding a tetraploid potato plant.

Further, the food includes: fresh potatoes, dried potatoes, frozen potatoes, French fries, potato chips, potato flour, or potato starch.

This application adopts the above technical solution and has the following beneficial effects: compared with the traditional method for solving potato self-incompatibility, this application has the following advantages:

(1) this application provides a StSCI protein for changing the self-incompatibility of diploid potato materials; the StSCI protein may relieve the cytotoxicity of multiple S-RNases and overcome the self-incompatibility defect of diploid potato materials, thereby realizing the breeding of diploid potato seeds;

(2) this application provides a vector containing the nucleotide sequence encoding the StSCI protein and the promoter, qualitatively editing the self-incompatibility gene, activating the StSCI gene, allowing the StSCI gene in a diploid potato to normally express StSCI protein, thereby overcoming the self-incompatibility of a diploid potato;

(3) this application provides a method for breeding a diploid potato, which utilizes the diploid potato material RH89-039-16 for self-crossing, thereby producing the diploid potato offspring and the diploid potato seeds with self-compatibility by self-crossing, wherein the self-compatibility is hereditary, and the obstacle of potato self-incompatibility is fundamentally solved;

(4) this application provides a method for breeding a diploid potato, which utilizes the diploid potato RH89-039-16 as the donor material for the StSCI gene, and the hybrid offspring do not produce undesirable traits, which is similar to the genetic background of the existing diploid potato cultivars.

DETAILED DESCRIPTION OF EMBODIMENTS

The technical solutions in the examples of the present application will be clearly and completely described with reference to the drawings in the examples of the present application. Obviously, the described examples are only a part of the examples of the present application, rather than all the examples. Based on the examples in this application, all of the other examples obtained by those of ordinary skill in the art without creative work shall fall within the protection scope of this application.

In the following examples, the diploid potato material RH89-039-16 is self-compatible, and the diploid potato material PI 225689 and S15-65 are self-incompatible.

Unless otherwise specified, all of the operation methods in the following examples belong to the prior art commonly used by those skilled in the art, and will not be explained repeatedly herein.

Example 1: StSCI Gene Position

The pollen of the diploid potato material RH89-039-16 is used to pollinate the originally self-incompatible diploid material PI 225689, and the seeds are harvested as the F1 generation. The self-compatibility traits of F1 generation plants are investigated, and it is found that self-compatible plants and self-incompatible plants respectively account for half of them, indicating that the self-compatibility gene in RH89-039-16 is in a heterozygous state, while RH89-039-16 shows self-compatibility traits, indicating that the gene for controlling the self-compatibility of RH89-039-16 is dominant, and this dominant gene is named as StSCI gene. The leaves of 40 self-compatible individual plants and 40 self-incompatible individual plants are respectively selected from the F1 generation, mixing and extracting the genomic DNA, then sequencing the genomic DNA of the two mixed pools.

Figure 1:
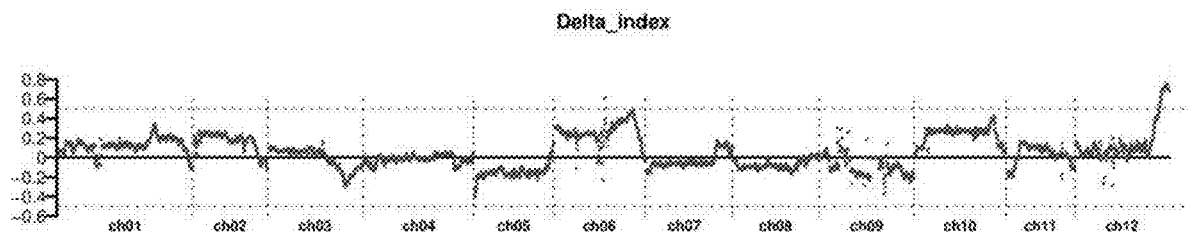
FIG. 1 is a plot showing the initial localization interval of the StSCI gene in Example 1.

The sequencing results are analyzed, and the difference between the SNP-index of the two pools is used to initially locate the StSCI gene in the 2.5 Mb interval at the end of chromosome 12, thereby obtaining the initial positioning interval of the StSCI gene (FIG. 1).

Genome resequencing is performed on the self-compatible diploid potato material RH89-039-16 and the self-incompatible diploid potato material PI 225689, and the molecular markers for StSCI gene positioning are developed according to the genomic sequence information of RH89-039-16 and PI 225689 in the initial positioning interval of in the StSCI gene. Since the StSCI gene is heterozygous in RH89-039-16, and is homozygous and recessive in PI 225689, the molecular markers to be linked to the StSCI gene and to be developed should also be heterozygous in RH89-039-16, and be homozygous in PI 225689. The molecular markers in the initial positioning interval are developed according to this principle, and the individual plants of F1 population are used as the positioning population to finely position the StSCI gene, finally positioning the StSCI gene in a 76 Kb interval. There are a total of 6 annotation genes in this interval. Using the sequence information of these 6 annotation genes, 6 pairs of quantitative primers are designed to respectively detect the expression levels of these 6 annotation genes, meanwhile the total plant RNA from pollen parts of RH89-039-16 and PI 225689 is extracted, and the expression levels of the annotated genes in pollen are detected by real-time fluorescent quantitative PCR (polymerase chain reaction), wherein three of them are highly expressed in pollen of RH89-039-16. Among the three genes highly expressed in pollen of RH89-039-16, the gene encoded as PGSC0003DMG400016861 is not expressed at all in pollen of PI 225689. This gene may be responsible for the self-compatibility of RH89-039-16 and the self-incompatibility of PI 225689, and it is a candidate gene of the StSCI gene.

A primer pair (represented by SEQ ID NO: 4 and SEQ ID NO: 5) for amplifying a region including the gene and the promoter is designed according to the annotated sequence information of the gene PGSC0003DMG400016861 in the DM genome, the genomic DNAs of RH89-039-16 and IP65C are respectively used as templates, and the PCR products are sequenced after PCR amplification. It is found that in the promoter region of this gene, RH89-039-16 has a 538 bp insert sequence as compared with PI 225689. This insert sequence is located 100 bp upstream of the initiation codon, the insert sequence includes an annotated promoter core element, and this sequence is the reason that the gene is expressed in RH89-039-16 but not in PI 225689.

The nucleotide sequence of the StSCI gene is represented by SEQ ID NO: 2.

The above inserted sequence is the promoter for regulating the StSCI gene, and its nucleotide sequence is represented by SEQ ID NO: 6.

Example 2: StSCI Gene Verification

In order to verify that gene PGSC0003DMG400016861 is the inducing gene responsible for the self-compatibility in RH89-039-16, a plant binary vector containing a 1245 bp of promoter region upstream of the initiation codon of the gene PGSC0003DMG400016861 in RH89-039-16 and a 3352 bp of full-length region of the gene is constructed by using pCAMBIA1301 as the backbone vector. With the aid of the *Agrobacterium* transformation system, the gene PGSC0003DMG400016861 in RH89-039-16 and its promoter are transferred into the originally self-incompatible diploid potato material S15-65 to obtain a complementary transgenic plant. Meanwhile an overexpression vector connecting the encoding region of gene PGSC0003DMG400016861 with CaMV35S as the promoter is constructed, and the same method is used to transfer it into the self-incompatible material PI 225689.

Figure 2:
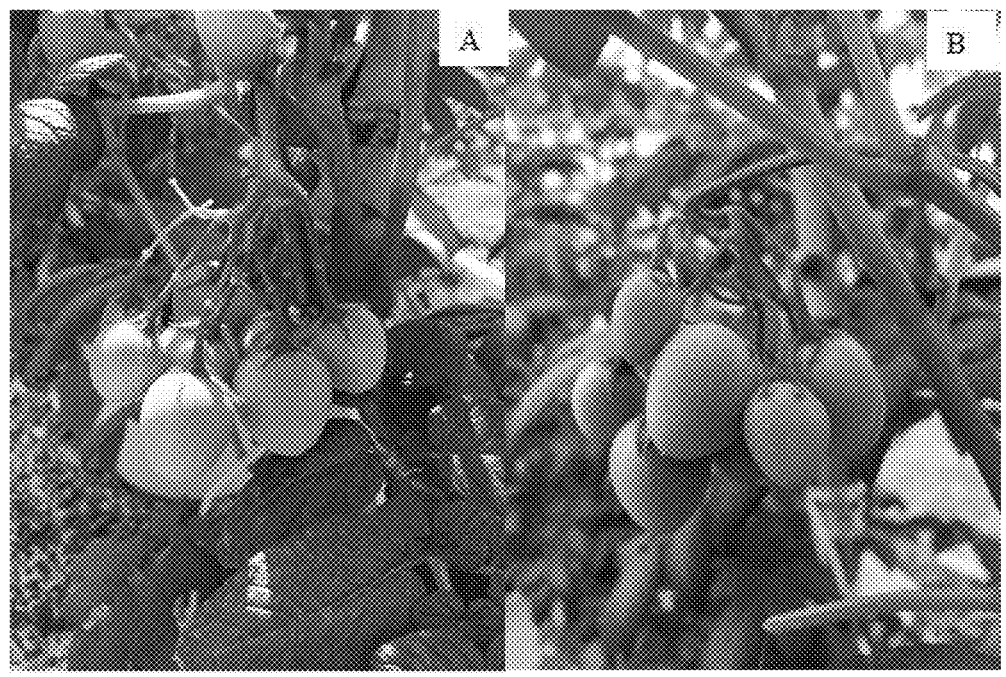
FIG. 2 are photos showing the identification of the self-compatibility phenotype of the diploid potato materials in Example 2, wherein panel A is the diploid potato material S15-65 having complementary expression of the StSCI gene, and panel B is the diploid potato material PI 225689 having overexpression of the StSCI gene.
Figure 3:
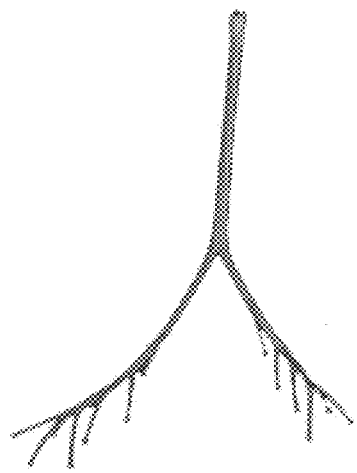
FIG. 3 is a diagram showing the identification of the self-compatibility phenotype of the self-compatible material RH89-039-16 after knocking out the StSCI gene.

Meanwhile, a gene knockout vector containing the gene PGSC0003DMG400016861 with 4 target positions is constructed by using CRISP/Cas9 technology, and the gene PGSC0003DMG400016861 is knocked out in the self-compatible RH89-039-16 material. It is found in the results in FIG. 2 that, the complementary expression or overexpression of the gene PGSC0003DMG400016861 in the self-incompatible material S15-65 may make the self-incompatible material S15-65 and PI 225689 become self-compatible, which are respectively shown in A and B of FIG. 2. After knocking out the gene PGSC0003DMG400016861 in the self-compatible material RH89-039-16, the originally self-compatible RH89-039-16 became self-incompatible (as shown in FIG. 3), indicating that the gene PGSC0003DMG400016861 is the StSCI gene responsible for self-compatibility of RH89-039-16.

Example 3: A Method for Producing a Self-Compatible Diploid Potato

The pCAMBIA1301 vector carrying the nucleotide sequence encoding the StSCI protein (SEQ ID NO: 2) and the promoter (SEQ ID NO: 3) is transferred into a diploid potato identified as self-incompatible by using *Agrobacterium* LBA440. As a result, it is found that the introduction of the above pCAMBIA1301 vector allows the StSCI gene in diploid potatoes to express the StSCI protein, thereby turning the self-incompatible diploid potato into self-compatible.

Example 4: A Method for Producing a Self-Compatible Diploid Potato

The pCAMBIA1301 vector carrying the nucleotide sequence encoding the StSCI protein (SEQ ID NO: 2) and the CaMV35S promoter is transferred into a diploid potato identified as self-incompatible by using *Agrobacterium* LBA440. As a result, it is found that the introduction of the above pCAMBIA1301 vector allows the StSCI gene in diploid potatoes to express the StSCI protein, thereby turning the self-incompatible diploid potato into self-compatible.

Example 5: A Method for Breeding a Diploid Potato by Self-Crossing

Diploid potato materials (such as RH89-039-16) capable of expressing the StSCI gene in pollen are self-compatible. Therefore, after RH89-039-16 enters the full flowering stage, the pollen from the stamens of RH89-039-16 is picked to spread on the stigma of the pistils of RH89-039-16 for self-pollination. Since RH89-039-16 is self-compatible, after self-pollination RH89-039-16 may produce seeds, thereby obtaining diploid potato seeds of RH89-039-16.

Example 6: A Method for Breeding a Diploid Potato by Hybridization

Diploid potato materials (such as RH89-039-16) capable of expressing the StSCI gene in pollen are self-compatible, while most diploid potato materials such as PI 225689 are self-incompatible. After the above RH89-039-16 and PI 225689 materials enter the full flowering stage, the pollen from the stamens of RH89-039-16 is picked to spread on the stigma of PI 225689 for hybridizing pollination. Half of the seeds produced by using genome recombination are capable of expressing StSCI gene, and thus they are self-compatible, thereby obtaining a self-compatible diploid potato material by hybridization.

The above descriptions are only preferred examples of this application, and are not intended to limit this application. Any modification, equivalent replacement, etc. made within the spirit and principle of this application shall be covered in the protection scope of this application.

---

What is claimed is:

1. A transgenic diploid self-compatible potato plant or part thereof, comprising (i) a heterologous promoter, and (ii) a polynucleotide sequence encoding a polypeptide comprising a sequence having at least 99% sequence identity to SEQ ID NO: 1,
wherein the heterologous promoter and the polynucleotide sequence are operably linked, the polynucleotide sequence is derived from a diploid potato, and the polypeptide is expressed.

2. The transgenic diploid self-compatible potato plant or part thereof of claim 1, wherein the part thereof is selected from the group consisting of seed, tuber, fruit, leaf, and flower.

3. The transgenic diploid self-compatible potato plant or part thereof of claim 1, wherein the diploid self-compatible potato plant is a hybrid.

4. The transgenic diploid self-compatible potato plant or part thereof of claim 1, wherein the heterologous promoter comprises the sequence shown in SEQ ID NO: 3, a CaMV35S promoter, a NOs promoter, or an Ocs promoter.

5. The transgenic diploid self-compatible potato plant or part thereof of claim 1, wherein the polypeptide comprises a sequence having 100% sequence identity to SEQ ID NO: 1.

6. The transgenic diploid self-compatible potato plant or part thereof of claim 5, wherein the polynucleotide comprises a sequence having 100% sequence identity to SEQ ID NO: 2.

7. A potato food comprising (i) a heterologous promoter, and (ii) a polynucleotide sequence encoding a polypeptide comprising a sequence having at least 99% sequence identity to SEQ ID NO: 1, wherein the heterologous promoter and the polypeptide sequence are operably linked, and the polynucleotide sequence is from a diploid potato.

8. The potato food of claim 7, wherein the food is selected from the group consisting of fresh potatoes, dried potatoes, frozen potatoes, French fries, potato chips, potato flour, and potato starch.

9. The transgenic diploid self-compatible potato plant or part thereof of claim 1, comprising (i) a promoter comprising the sequence shown in SEQ ID NO: 3, a CaMV35S promoter, a NOs promoter, or an Ocs promoter; and (ii) a polynucleotide sequence encoding the polypeptide shown in SEQ ID NO: 1;

wherein the promoter and the polynucleotide sequence are operably linked, and the polypeptide is expressed.

\* \* \* \* \*